United States Patent [19]
Swartz

[11] Patent Number: 5,798,393
[45] Date of Patent: Aug. 25, 1998

US005798393A

[54] BETAXOLOL HYDROCHLORIDE FOR THE TREATMENT OF ANXIETY DISORDERS

[76] Inventor: Conrad Melton Swartz, P.O. Box 2952, Greenville, N.C. 27836-0952

[21] Appl. No.: 627,685

[22] Filed: Apr. 2, 1996

[51] Int. Cl.$^6$ .................................................. A61K 31/135
[52] U.S. Cl. ............................................................ 514/652
[58] Field of Search ................................................ 514/652

[56] References Cited

U.S. PATENT DOCUMENTS 5,525,347   6/1996   Kellner et al.

OTHER PUBLICATIONS

Le Van et al, Therapie, vol. 43, No. 6, pp. 451–456, 1988.
Thomas, C. L., Ed., Taber's Cyclopedia Medical Dictionary, 17th Edition, pp. 129 and 129, 1993.
Turner, Derwent Drug File Abstracts, Abstract No. 89-09926, 1989.

*Primary Examiner*—William R. A. Jarvis
*Attorney, Agent, or Firm*—Eliot S. Gerber

[57] ABSTRACT

The compound betaxolol has the chemical formula:

1-[4[2-cyclopropylmethoxy)ethyl]phenoxy]-3-[1-methylethyl)amino]-2-propanol.

It is administered, preferably orally, once per day in 4–12 mg. tablets for the treatment of symptoms of anxiety disorder in human patients. Such symptoms include those present in Generalized Anxiety Disorder (GAD), which include somatic symptoms such as panic, palpitations and pounding heart.

2 Claims, No Drawings

BETAXOLOL HYDROCHLORIDE FOR THE TREATMENT OF ANXIETY DISORDERS

FIELD OF THE INVENTION

The present invention relates to medicine and more particularly to the administration of pharmaceuticals to relieve mental disorders.

BACKGROUND OF THE INVENTION

Anxiety symptoms are common, and they pose risks to the person who suffers such symptoms as well as his family and co-workers. The psychiatric mental condition (diagnosis) of Generalized Anxiety Disorder (GAD) is an archetype of problematic anxiety. According to the American Psychiatric Association's Diagnostic and Treatment Manual of Psychiatry, 4th edition (DSM-4) the core symptoms of GAD include feelings of being on edge or easily upset, easily fatigued, irritability, argumentativeness or easy anger, decreased concentration or instances of mind blanking, muscle tension, and sleep disturbance consisting of difficulty in falling asleep or oversensitive awakening. GAD is considered to be present when at least several of these symptoms are present. These symptoms are commonly associated with a fluctuating mood, which can include a sense of sadness or desperation, and feelings of being overwhelmed or victimized. In some patients, anxiety is also associated with a variety of body-related (or "somatic") symptoms, which are themselves unpleasant and distressing.

These somatic symptoms include panic; palpitations, pounding heart or accelerated heart rate; sweating; shaking or trembling; shortness of breath or smothering; feelings of choking; chest discomfort; tightness or pain; nausea or abdominal distress; feelings of unsteadiness, lightheadedness, faintness or similar dizziness; feeling of unreality or depersonalization (detachment from self); fears of losing control or of going crazy; fears of dying; sensations of numbness or tingling, typically in the fingers or around the lips; cold sweats, chills or hot flushes; tension headache; gas pains; intestinal spasms; restless agitation; dry mouth; and decreased tolerance for physical exertion.

Regarding the frequency of anxiety disorders, recent epidemiologic surveys indicate that the 12-month prevalance of the anxiety disorders and Panic Disorder is 13%, which is greater than the 10% prevalance of major depression. Addition to this of Adjustment Disorder with Anxiety may increase the prevalance of problematic anxiety to over 20%.

The suffering and risks associated with anxiety disorders make treatment important. Anxiety disorder symptoms lead to premature death; they are associated with a 350%–500% excess of sudden cardiac death and 200% excess of fatal coronary heart disease in males, seen in both a general population and the medical professions. Similarly, in depressed patients higher levels of anxiety were associated with higher suicide rates. Job-related stress and intimidation are associated with anxiety, i.e., adjustment disorder is associated with anxiety. Frequent sufferers include junior and mid-level personnel in a hierarchy, including professionals and managers. Violent acts committed in anger by disgruntled employees against co-workers or supervisors are notorious examples of job-related anxiety, but these are surely the "tip of the iceberg" as a sign of the suffering and risks associated with anxiety.

Betaxolol hydrochloride (referred to as "betaxolol" ™) is a chemical that blocks beta-adrenergic receptors on cell membranes in the body, and it is accordingly described as a beta-blocker. Betaxolol is largely specific to subtype 1 of beta-adrenergic receptors. The chemical name of betaxolol is 1[4-[2-(cyclopropylmethoxy)ethyl]phenoxy]-3-[(1-methylethyl)amino]-2-propanol and includes its pharmaceutically acceptable acid addition salts, preferably the addition salt of hydrochloride, and its molecular formula is $C_{18}H_{29}NO_3$ HC1. It is a white crystalline powder that is soluble in water and ethanol. It is available from ALCON LABORATORIES, Fort Worth, Tex., U.S.A., and Kayersberg, France.

Betaxolol has been used for the management of hypertension, that is, the reduction of systolic and disatolic blood pressures; however, many medications, including diuretics, reduce blood pressures without providing a clinical antianxiety action. A search of the MEDLINE and PSYCINFO computer indexes of the medical and psychiatric literature revealed no mention of betaxolol in the treatment of anxiety, panic, depression, stress, impulse control or adjustment disorder; or is such a use mentioned in Medical Economics' Physician's Desk Reference (PDR) in the statement by the company that distributes betaxolol for the management of hypertension.

Beta-blockers are generally disregarded in the treatment of anxiety disorders. This disregard apparently resulted from several misperceptions in the medical literature. One error is the claim that beta-blockers cause depression (e.g., Hayes & Schultz 1987); this assertion was never established by systematic measurement and indeed was recently disproven (Bright & Everitt 1992). Another error followed several studies that failed to find an antianxiety effect of the beta-blocker atenolol (e.g., Rickels et al 1986), specifically that the ineffectuality of atenolol indicates that the entire group of beta-blockers is ineffectual (Lydiard et al 1988).

U.S. Pat. Nos. 4,252,984 and 4,760,182 relate to methods for producing betaxolol. U.S. Pat. No. 5,378,475 for "Sustained Release Drug Delivery Devices", at column 5, line 51, mentions that the beta blocker betaxolol may be administered using the device of that patent. U.S. Pat. No. 5,290,561 entitled "Single Layer Transdermal Drug Administration System", at column 37, line 42, mentions that betaxolol may be administered by the transdermal patch of that patent. These patents are incorporated by reference herein.

SUMMARY OF THE INVENTION

Absorption of betaxolol taken by mouth is typically complete. The average elimination half-life of betaxolol from the human body is about 18 hours and is 50% to 100% higher in elderly individuals. It is removed from the body in a two-part process; first it is chemically transformed in the liver, and then the transformed products are put in the urine by the kidneys.

Blockage of beta-adrenergic receptors decreases the effects of internal secretions of the hormone epinephrine (also called adrenaline) and related hormones, which activate this receptor. Epinephrine stimulates the sympathetic nervous system and increase feelings of panic, fear, anxiety or anger. This blockage decreases unpleasant bodily sensations associated with anxiety fear and stress, which can be further irritating and stressful to patients.

As mentioned above, the beta-blocker atenolol was not found to have a large antianxiety effect. However, there is a crucial difference between atenolol and betaxolol. Betaxolol penetrates the blood-brain barrier, and so can enter the brain, and atenolol does not. Studies of agents that do not enter the brain, including atenolol, do not necessarily apply to betaxolol, metropolol and propranolol, which do enter the brain. As an illustration of this; metoprolol, but not atenolol or a placebo, decreased anxiety ratings from arithmetic challenge, although both beta-blockers equally reduced the heart rate (Schweizer et al, 1991). Similarly, an animal study found that propranolol was far more potent than atenolol (Durel et al 1986), consistent with penetration of the brain by propranolol. Nevertheless, a few studies have suggested some effectiveness of atenolol (Gorman & Gorman 1987), so that beta-adrenergeric blockage outside the brain might have some small antianxiety benefits.

DETAILED DESCRIPTION OF THE INVENTION

In accordance with the present invention, betaxolol is orally administered to decrease the effects of internal secretions of hormones such as epinephrine, which stimulate the sympathetic nervous system and increase feelings of panic, fear, anxiety or anger. This blockage decreases unpleasant bodily sensations and perceptions associated with anxiety, fear, stress and panic. These include palpitations, pounding heart or accelerated heart rate; ventricular premature contractions; sweating; shaking or trembling, shortness of breath or smothering; feelings of choking, chest discomfort, tightness or pain; nausea or abdominal distress; feelings of unsteadiness, lightheadedness, faintness or similar dizziness; feelings of unreality or depersonalization (detachment from self); fears of losing control or of going crazy; fears of dying; sensations of numbness or tingling, especially in the fingers or around the lips; cold sweats, chills or hot flushes; tension headache; gas pains; intestinal spasms; restless agitation; aggressive agitation; dry mouth; rapidly variable mood; feelings of nervousness; difficulty in concentration; early and easy fatigue; suicidality; irritability; and argumentativeness.

Patients with any mental disorder in which these sensations and perceptions are a source of substantial distress or impairment may experience a decrease in these sensations and perceptions from a suitable dose of betaxolol. These mental disorders include the Anxiety Disorders, the Depressive Disorders, the Stress Disorders, the Impulse Control Disorders, and the Adjustment Disorders. Some specific diagnoses in these groups are Generalized Anxiety Disorder, Panic Disorder, Adjustment Disorder with Anxiety, Adjustment Disorder with Mixed Anxiety and Other Features, Acute Stress Disorder, Post-Traumatic Stress Disorder, Simple Phobia and Major Depressive Disorder.

Anxiety disorders (such as Generalized Anxiety Disorder and Panic Disorder) are usually treated with an antidepressant of tricyclic type (such as Tofranil™ brand of imipramine), MAO-inhibitor type (such as Nardil™ brand of phenelzine), or serotonin-reuptake inhibitor (SRI) type (such as Prozac™ brand of fluoxetine). They are sometimes treated with the putative antianxiety agent BuSpar™ (buspirone), or with a benzodiazepine sedative such as Xanax™ (alprazolam), Ativan™ (lorazepam), Valium ™ (diazepam), or Klonopin™ (clonazepam). Beta-blockers such as betaxolol are chemically different from these other agents and betaxolol has advantages over each of these other types of medication, as explained in detail below.

1. Our tests have shown that betaxolol relieves anxiety and panic symptoms much faster than antidepressants and BuSpar™ do. Betaxolol works in 1 to 3 days, compared to 2–12 weeks or longer with BuSpar™ or antidepressants. Further, BuSpar™ does not mitigate panic symptoms. This advantage should lead to shorter hospital stays, less time needed from doctors, more rapid relief and greater attractiveness to the patient with consequent better compliance with the prescribed dosage.

2. Betaxolol has rapid cardioprotective action in patients with anxiety-induced arrhythmia or coronary artery spasm. Benzodiazepine sedatives can provide this benefit temporarily and the other pharmaceutical agents do not provide it at all.

3. There is no tolerance, dependence or potential for abuse with betaxolol, although these effects are problematic with benzodiazepine sedatives.

4. Our tests have shown that betaxolol has persistent efficacy against panic attacks and anxiety. Although benzodiazepine sedatives work quickly, they lose effectiveness after a few weeks as a result of tolerance by the body.

5. Betaxolol causes no impairment of cognitive function or physical performance, and rather tends to improve cognitive function. In contrast, benzodiazepines are notorious for decreasing cognition and performance skills including memory, learning and reaction time. Further, benzodiazepines amplify impairment from the consumption of beverage alcohol, and the combination risks death from suppression of respiration. In comparison, betaxolol does not increase the health risks of alcohol beverage consumption. Tricyclic antidepressants cause substantial cognitive impairment because of their strong anticholinergic activity.

6. Betaxolol causes no disturbance in appearance, manner and judgment. In contrast, benzodiazepine sedatives coarsen and disinhibit the personalty. Benzodiazepines, tricyclic antidepressants and SRI antidepressants can cause drowsiness.

7. Betaxolol causes little, if any, interference with sexual function in the recommended doses of 5 to 10 mg/day. All the other medications noted are notorious for interfering with sexual function.

8. Betaxolol causes no blood pressure elevation or tachycardia; risks of dangerous blood pressure elevation have minimized the use of MAO-inhibitors.

9. Betaxolol has no anticholinergic effects, as tricyclic antidepressants do; these effects are troublesome and they include urinary retention, dry mouth, glaucoma, tachycardia and constipation.

10. Betaxolol has none of the gastrointestinal side-effects of SRI agents such as Prozac, which include nausea, headache, diarrhea and intestinal spasms. Indeed, betaxolol calms intestinal spasms and prevents headache. Antipsychotic sedatives are even less attractive because they impair initiative-taking, set-shifting, problem solving and exploratory behavior; they also cause involuntary movements, block emotional communication, impair grooming and recognition of social cues, and cause drowsiness.

11. Betaxolol does not strongly block the elimination of other drugs, which is a troublesome action of the SRI antidepressants, particularly Prozac and Paxil.

Betaxolol has a particular distinction that makes it more desirable than other commercially available beta-blockers. Among the beta-blockers that enter the brain, it is eliminated most slowly. Because of its slow elimination, betaxolol gives consistent effects throughout the day and night without the rebound effects that occur during troughs of blood concentration (shown as insomnia or intermittent anxiety), or discontinuation (e.g., angina), as seen with short half-life agents such as propranolol or metoprolol. Even sustained-release preparations of propranolol can produce insomnia, by rebound, if the release is exhausted during hours of sleep, because propranolol is eliminated so rapidly. Rapid disappearance of propranolol and beta-adrenergic rebound hyperactivity might dispose patients to sudden cardiac death, especially patients prone to coronary vasospasm (Mulcahy 1994). Further, a once-daily dosing of betaxolol would produce better compliance than the more frequent dosing required with short-acting drugs.

Once-daily morning dosage of betaxolol also coincides with circadian rhythms, which can be influenced by beta-blockers. Specifically, both beta-blockers and bright light suppress melatonin secretion. Giving betaxolol early in the morning and accordingly suppressing melatonin levels at that time parallels bright-light therapy for Seasonal Affective Disorder (Winter Depression). This should help to preserve day-night rhythms to avoid insomnia and uncomfortable bodily feelings similar to jet lag, including the same symptoms of GAD mentioned above.

The other beta-blockers that are slowly eliminated, nadolol and atenolol, do not cross the blood-brain barrier and so do not enter the brain. Betaxolol's beta-blockage is relatively specific to subtype 1 receptors (Cooper et al 1990; Tyrer et al 1991) which is the kind that is associated with anxiety and is present in the brain. Subtype 2 receptors, which are present in the lungs and act to dilate air passageways, are minimally blocked by betaxolol; this is a virtue because betaxolol is less likely to obstruct pulmonary function. The absence of the intrinsic sympathomimetric activity, caused by acebutolol, alprenolol, oxprenolol, penbutolol and pindolol, give betaxolol greater effect against cardiac arrhythmias, including tachycardias and ventricular premature constructions, and against other somatic symptoms associated with excessive sympathetic nervous system activity, e.g., tremors, bowel spasms and agitation.

THE EFFECTS OF BETAXOLOL ON ANXIETY—EXAMPLES

A test, with informed consent, was conducted in which betaxolol was administered to over 16 inpatients and 14 outpatients with GAD, Panic Disorder or Adjustment Disorder with anxiety. All had at least one somatic manifestation of anxiety. All of the 16 inpatients had failed to respond to trials of antidepressants, and 4 of these had also received antipsychotics, which suggests severe illness. Each patient was distinctly ill. All inpatients (16/16) improved within 2 days on betaxolol. Of the outpatients, 12/14 (86%) responded to betaxolol for GAD or Adjustment Disorder with Anxiety; the other two patients were unable to tolerate betaxolol, so that all 12 patients who could tolerate it responded to it. Of the 5 outpatients with panic disorder, all showed complete relief of panic attacks with betaxolol. Of the 12 patients who responded to betaxolol, all showed some good effects on 5 mg/day and 3 benefited further by a dosage increase to 10 mg/day. Most of the inpatients and 9 of the outpatients had concurrent obsessive-compulsive personality disorder.

Rapid improvement from betaxolol typically caught the patient's interest; although some patients looked obviously better yet were unaware of their improvement until discussed and reviewed by the doctor. Below is a capsule description of eight middle-class patients for whom the effects of betaxolol were prominent.

1. A 58-year-old Caucasian woman experienced debilitating panic attacks 2–12 times/day following a one-car automobile collision 6 weeks prior. She wore body shell braces to help heal her multiple bone fractures. Betaxolol 5 mg/day decreased panic attacks 50% within 3 days; a dose increase to 10 mg/day stopped the panic attacks entirely after another day, and also stopped fears of more panic attacks. The patient became able to relax, pace herself and cope well with the body shell braces. She said "this is the best medicine I've ever taken" and she denied any side effects. Her diagnosis was Adjustment Disorder with Anxiety.

2. A 24-year-old Caucasian male college student experienced severe tension headaches (taking up to 6000 mg Tylenol/day), frequent angry thoughts, jumpiness, impatience, racing heart, insomnia, poor concentration, general slowness and episodes of impulsive anger since being mugged 2 months earlier. His injury included a depressed skull fracture and he had total loss of income and inability to continue school, all of which intimidated him. Betaxolol 10 mg/day immediately and entirely relieved the anxiety symptoms, and he even slept well. His diagnoses were Major Depression associated with Traumatic Brain Injury and Adjustment Disorder with Anxiety.

3. A 60-year-old Caucasian male ex-lawyer was hospitalized for suicidality with longstanding chronic fatigue, fibromyalgia, insomnia and insistent claims of depressed feelings. He had failed to improve with buspirone, amtitriptyline, fluoxetine, sertraline, bupropion, phenelzine, chlorpromaxine, traxodone, triaxolam, and numerous psychotherapies. He took metoprolol 100 mg twice daily and Lotensin 20 mg/day. His psychomotor activity was normal and speech fluent, and he frequently demanded company and attention. His blood pressure was high several times a day. Lopressor was replaced with betaxolol 10 mg twice daily; within two days he admitted less anxiety, less fatigue, better mood and better sleep, and his blood pressure showed no elevations. This improvement persisted through his remaining 10 days in the hospital. His diagnoses were Generalized Anxiety Disorder and Obsessive-Compulsive Personality Disorder.

4. A 35-year-old Caucasian woman with symptoms of Generalized Anxiety Disorder, of severe intensity, and numerous daily panic attacks, showed relief of all symptoms with betaxolol. Her panic attacks had been dominated by episodic sensations of heat on her skin, dizziness, bowel spasms, fear, trembling and nausea. Besides these episodes, she continually felt wound up, easily startled, fatigued, incapable of concentration and irritable; she had frequent tension headaches and she wakened from sleep too easily. She forgot betaxolol when she took a trip; three days later she had the first panic attack since starting betaxolol. With resumption of the betaxolol there were no more panic attacks, although anxiety symptoms reappear each month prior to her menstrual periods and then decrease. Her diagnoses were Panic Disorder and Generalized Anxiety Disorder.

5. A 44-year-old formerly alcoholic African-American woman who had all symptoms of Generalized Anxiety Disorder of severe intensity and typically had 2 panic attacks daily, experienced complete relief after 2 days of betaxolol. Her panic attack symptoms had included pounding heart, sweating, dyspnea, choking, dizziness, depersonalization, fear, paresthesias, and waves of heat. Her anxiety symptoms were the same as with the previous patient. She had a history of hayfever, but had denied asthma. She took betaxolol for 2 weeks; during this time she felt no panic or anxiety, but found herself wheezing and short of breath when she went outside. Nevertheless, she did not contact me to complain until a painful rash appeared. A day after stopping the betaxolol the rash and wheezing disappeared. The anxiety returned the next day with an urge to drink; after another week she was brought to the hospital intoxicated with beverage alcohol. This was her first drunkenness for 6 months. Her diagnoses were Panic Disorder, Generalized Anxiety Disorder, and Alcoholism.

6. A 68-year-old Caucasian woman was referred by another psychiatrist because of persistent unhappiness for 20 years. She showed anxiety symptoms were like those of patients #4 and #5, but with back pain and without panic attacks. On the 4th day of taking betaxolol 5 mg daily she revealed that within 2 days of starting betaxolol she felt calm, had stopped shaking, and her back pain had diminished strikingly. Only on specific questioning did she admit that betaxolol had made breathing more difficult, and she had started wheezing. The anxiety returned within a few days of discontinuation of betaxolol. Her diagnosis was Generalized Anxiety Disorder.

7. A 36-year-old Caucasian male nurse described a 7-year history of bowel spasms and gas pain, irritability and tension, for which he took paroxetine. Whenever he tried to stop the paroxetine these symptoms returned. He started betaxolol 5 mg/day; after 3 days he discontinued the paroxetine and continued in good spirits. He then discontinued the betaxolol and found that the irritability and tension returned; it disappeared again when he restarted the betaxolol. In conjunction with a misunderstanding he was removed from his job; he reported that his mood continued well and he was petitioning to regain his job. He said that he was surprised that he was not incapacitated by anxiety from this stress; he attributed his good mood and good functioning to the betaxolol. His diagnosis is Generalized Anxiety Disorder; in addition, the betaxolol prevented an episode of Adjustment Disorder with Anxiety.

8. A 50-year-old Caucasian female nurse emphatically described herself as a lifelong worrier, with poor concentration and mind-blanking that interferes with her activities and annoys her; variable mood over the day, restlessness and edginess, early fatigue in the day, and problematic muscle tension with band-like tension headaches, neck aches, back aches. She also complained of constipation, stress-associated palpitations typically twice daily, heartburn, and middle- and late-insomnia. She was able to sleep by taking doxepin 25 mg at bedtime, but gained excessive weight on it and did not obtain relief of her other symptoms. She was on edge, hyperalert and emotionally intense. She started betaxolol 5 mg/day. On a visit two weeks later she appeared relaxed and calm; she reported good concentration and mood, no mind-blanking, no restlessness, and no headaches. She told of taking up sewing. The Sinequan™ was stopped and the benefits continued, but betaxolol was increased to 10 mg/day in view of easy awakening. A month later she was found to have breast cancer and she arranged for surgery. She was surprised and pleased to find that her mood was stable, her concentration was good, she was not upset, and she was taking the events calmly, which was not typical for her. She attributed this to betaxolol. On followup 3 months later she had had cancer surgery and was taking chemotherapy; she confirmed that the benefits of betaxolol were continuing and were important to her, and she was insistent on continuing. Her diagnosis is Generalized Anxiety Disorder.

Betaxolol, either by itself or in combination with a carrier, may be administered subcutaneously, intradermally, orally, parenterally, intraperitoneally, intravascularly, or by any other suitable means. The particular manner of administration will be selected in order to ensure that the drug or drugs are able to be directed to the site of desired action in an effective dosage.

Betaxolol can be formulated in conventional manners employing a physiologically or pharmacologically acceptable carrier. Such carriers include solutions where the drug may be suspended (optionally employing a surfactant or emulsifier) or dissolved. The drug is available formulated as a tablet, capsule or the like. Orally administratable tablets and capsules containing from 5–95% active ingredient are suitable. Parenteral compositions containing 1–100 mg/ml can readily be prepared.

The dosage of the subject compounds will generally be at least about 1.0 and not more than about 20 mg per day in single or multiple doses, usually from about 3–20 mg/day and most preferably 4–12 mg/day. The treatment course can be given for a day, a few days, weeks, months, or years, depending upon the effectiveness of the course of treatment or the refractory nature of the disease.

Betaxolol can be administered in conjunction with, either in the same formulation or in a separate formulation, other drugs which act in cooperation with the drugs of the subject invention or may be employed to provide for various supportive propylaxis or therapeutic capabilities.

The invention now being fully described, it will be apparent to one of ordinary skill in the art that many changes and modifications may be made thereto without departing from the spirit or scope of the appended claims.

References Cited

Bright R A, Everitt D E. Beta-blockers and depression. Evidence against an association. JAMA 1992;267:1783–7.

Cooper S J, Kelly C B, McGilloway S, Gilliland A. Beta 2-adrenoceptor antagonism in anxiety. European Neuropsychopharm 1990; 1:75–7.

Durel, L A, Krantax D A, Barrett J E. The antianxiety effect of beta-blockers on punished responding. Pharm Biochem Behav 1986;25:371–4.

Hayes P E, Schulz S C. Beta-blockers in anxiety disorders. J Affective Dis 1987;13:119–30.

Lydiard R B, Roy-Byrne P P, Ballenger J C. Recent advances in the psychopharmacological treatment of anxiety disorders. Hosp Comm Psychiatry 1988;39:1157–65.

Mulcahy D. Circadian variations in cardiovascular disease: implications for treatment. Brit J Clin Pract Symp Suppl 1994;73:31–6.

Rickels K, Csanalosi I B, Chung H R, Avallone M F et al. The beta-blocker atenolol in anxiety: a controlled study. Curren Ther Res 1986;40:149–55.

Schweizer R, Roth W A T, Elbert T. Effect of two beta-blockers on stress during mental arithmetic. Psychopharmacology 1991;105:573–77.

Tyrer P, Marsden D, Ferguson B, Murphy S, et al. Clinical and humora effects of beta-blockade with ICI 118,551 in the general neurotic syndrome. J. Psychopharm 1991;5:238–42.

What is claimed is:

1. A method of relieving the symptoms of anxiety of Generalized Anxiety Disorder, Panic Disorder, Post Traumatic Stress Disorder, or Adjustment Disorder with Anxiety comprising administering to a patient an anxiolytically effective amount of the compound betaxolol or a pharmaceutically acceptable addition salt thereof.

2. The method of claim 1 wherein the compound is administered orally in the amount of 3–20 mg/day.

* * * * *